(12) United States Patent
Ishii

(10) Patent No.: US 8,456,562 B2
(45) Date of Patent: Jun. 4, 2013

(54) IMAGE PICKUP UNIT

(75) Inventor: Hiroshi Ishii, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/372,593

(22) Filed: Feb. 14, 2012

(65) Prior Publication Data

US 2012/0182458 A1 Jul. 19, 2012

Related U.S. Application Data

(63) Continuation of application No. PCT/JP2010/058120, filed on May 13, 2010.

(30) Foreign Application Priority Data

Sep. 3, 2009 (JP) ................................. 2009-203974

(51) Int. Cl.
*H04N 5/225* (2006.01)
*A61B 1/05* (2006.01)

(52) U.S. Cl.
USPC .............. 348/335; 348/75; 396/17; 600/112; 600/170

(58) Field of Classification Search
USPC ................. 348/65, 66, 67, 68, 71, 72, 73, 74, 348/75, 76, 335, 340, 344; 600/109, 112, 600/129, 130, 160, 170, 171, 172; 396/17; 359/833, 514, 678
See application file for complete search history.

(56) References Cited

U.S. PATENT DOCUMENTS

| 4,727,859 A * | 3/1988 | Lia ................................ 600/170 |
| 5,253,638 A * | 10/1993 | Tamburrino et al. .......... 600/170 |
| 6,537,209 B1 * | 3/2003 | Pinkhasik et al. ............ 600/170 |

(Continued)

FOREIGN PATENT DOCUMENTS

| JP | 09-149883 | 6/1997 |
| JP | 09-262207 | 10/1997 |
| JP | 2005-121967 | 5/2005 |
| JP | 2006-201796 | 8/2006 |
| JP | 2006-227378 | 8/2006 |
| JP | 2007-094359 | 4/2007 |

OTHER PUBLICATIONS

International Search Report dated Jun. 15, 2010 issued in PCT/JP2010/058120.

*Primary Examiner* — John Villecco
(74) *Attorney, Agent, or Firm* — Scully, Scott, Murphy & Presser, P.C.

(57) ABSTRACT

In an image pickup unit, a first optical system holding frame has a hole axis orthogonal to an optical axis of photographing light made incident on a first object lens group, and a through-hole portion through which a second optical system holding frame can be inserted and arranged is formed in the first optical system holding frame and the first optical system holding frame and the second optical system holding frame are set relatively movable in a direction orthogonal to the optical axis of the photographing light made incident on the first object lens group and the second optical system holding frame and a third optical system holding frame are set relatively movable in a direction along the optical axis of the photographing light made incident on a solid-state image pickup device such that predetermined optical performance adjustment can be performed during assembly.

7 Claims, 11 Drawing Sheets

U.S. PATENT DOCUMENTS

| | | | |
|---|---|---|---|
| 7,713,189 B2* | 5/2010 | Hanke | 600/109 |
| 8,314,835 B2* | 11/2012 | Kanzaki et al. | 348/75 |
| 2003/0040657 A1* | 2/2003 | Yamaya et al. | 600/107 |
| 2003/0092966 A1* | 5/2003 | Schara et al. | 600/173 |
| 2005/0191046 A1* | 9/2005 | Dehmel et al. | 396/17 |
| 2006/0252995 A1* | 11/2006 | Hoeg et al. | 600/173 |
| 2009/0160935 A1* | 6/2009 | Rovegno | 348/65 |
| 2011/0221878 A1* | 9/2011 | Kitaoka et al. | 348/66 |

* cited by examiner

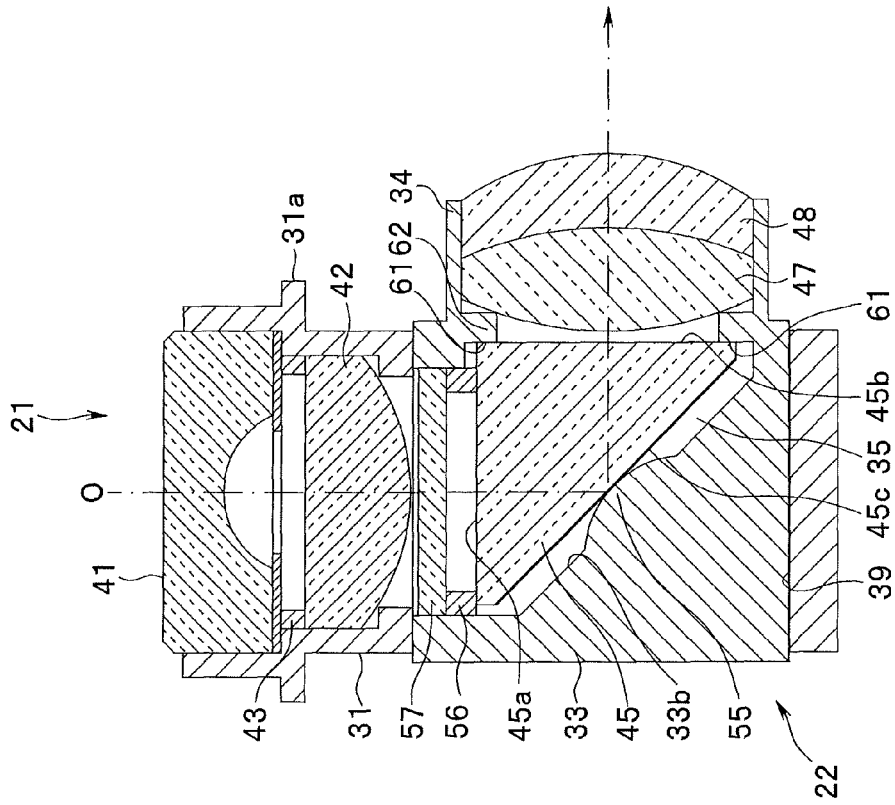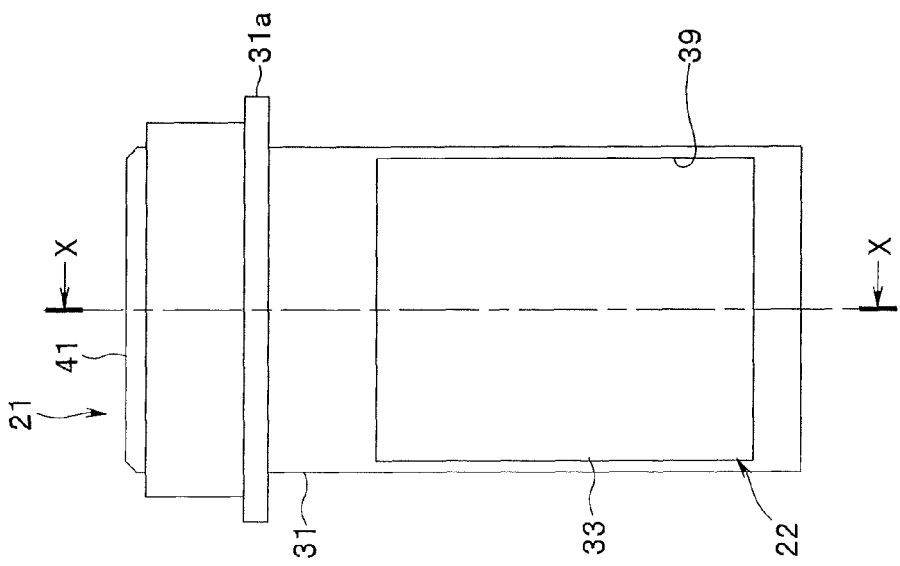

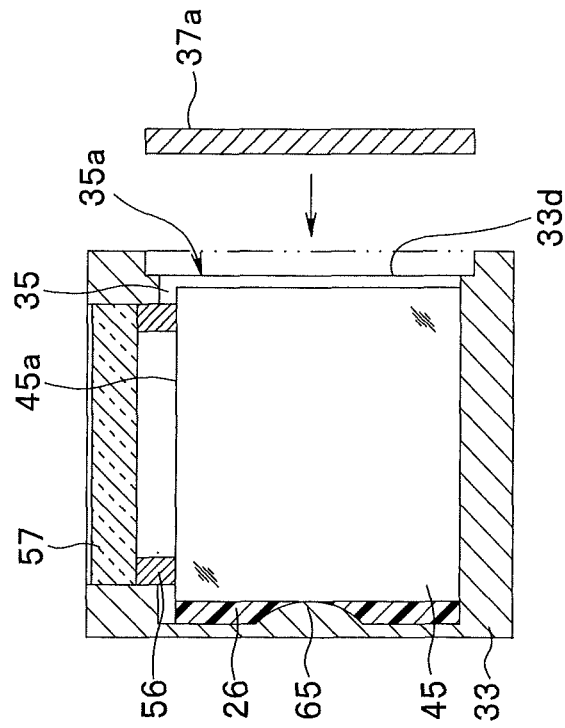
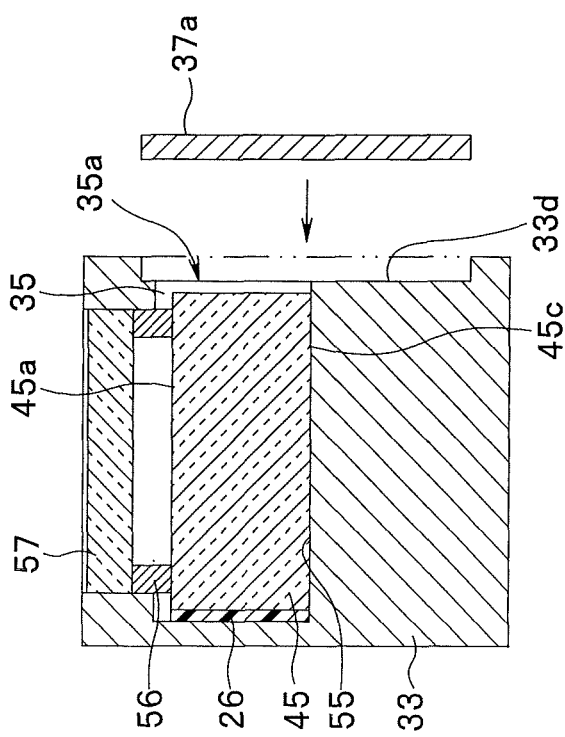

IMAGE PICKUP UNIT

CROSS REFERENCE TO RELATED APPLICATION

This application is a continuation application of PCT/JP2010/058120 filed on May 13, 2010 and claims benefit of Japanese Application No. 2009-203974 filed in Japan on Sep. 3, 2009, the entire contents of which are incorporated herein by this reference.

BACKGROUND OF THE INVENTION

1. Field of the Invention

The present invention relates to an image pickup unit that is used mainly in an endoscope apparatus of a side-view type, an oblique-view type, or the like and includes a prism that converts an optical path of photographing light.

2. Description of the Related Art

In recent years, endoscopes have been widely used in medical fields and industrial fields. As for an endoscope in the past, a mainstream is an endoscope in which an image guide is used and with which a user can observe an inside of a body cavity of a patient, an inside of a jet engine, or the like in an eyepiece section that the user looks into.

Further, as an endoscope in these days, an electronic endoscope apparatus emerges that incorporates an image pickup unit, photographs an inside of a body cavity of a patient, an inside of a jet engine, or the like, and displays an endoscope image on a display device such as an external monitor. As such an electronic endoscope, according to uses, there are a front-view type endoscope, an observation direction of which is a direction along a long axis of an insertion section, and a side-view type (oblique-view type) endoscope apparatus, an observation direction of which is a direction having a predetermined angle with respect to the long axis of the insertion section.

In the side-view type (oblique-view type) endoscope apparatus, an image pickup unit that picks up an image in the observation direction having the predetermined angle with respect to the long axis of the insertion section is incorporated. In the image pickup unit, a prism, which is an optical path converting optical component, for reflecting observation light and converting the observation direction disclosed in, for example, Japanese Patent Application Laid-Open Publication Nos. 2005-121967, 2006-201796, and 09-262207 is provided.

SUMMARY OF THE INVENTION

In order to attain the object, an image pickup unit according to an aspect of the present invention includes: a first optical system holding frame configured to hold a first object lens group; a second optical system holding frame fit in the first optical system holding frame and configured to hold a second object lens group and store a prism that reflects photographing light made incident on the first object lens group and subjects the photographing light to optical path conversion; and a third optical system holding frame fit in the second optical system holding frame and configured to hold an image pickup device that detects the photographing light subjected to the optical path conversion by the prism and photoelectrically converts the photographing light. The first optical system holding frame has a hole axis orthogonal to an optical axis of the photographing light made incident on the first object lens group, and a through-hole portion through which the second optical system holding frame can be inserted and arranged is formed in the first optical system holding frame, and the first optical system holding frame and the second optical system holding frame are set relatively movable in a direction orthogonal to the optical axis of the photographing light made incident on the first object lens group. The second optical system holding frame and the third optical system holding frame are set relatively movable in a direction along the optical axis of the photographing light made incident on the solid-state image pickup device. Predetermined optical performance adjustment can be performed during assembly.

An image pickup unit according to another aspect of the present invention includes: a prism unit including a prism storage frame, in which a prism is stored, and configured to receive incidence of photographing light and convert an optical path with the prism and emit the photographing light; a prism storing section formed in the prism storage frame and including an opening portion on a side portion of the prism storage frame such that the prism can be stored from a direction orthogonal to an optical axis of the photographing light and emitting light; and a cover body fit in the prism storage frame to cover the opening portion.

According to the present invention explained above, it is possible to improve efficiency of productivity and assemblability to be higher than in the past and provide an image pickup unit including a prism, yield of which is improved.

BRIEF DESCRIPTION OF THE DRAWINGS

FIG. 9 is a front view relating to a second embodiment of the present invention and showing a configuration of an image pickup unit;

FIG. 10 is a sectional view relating to the second embodiment and showing the configuration of the image pickup unit along X-X in FIG. 9;

FIG. 11 is a sectional view of a prism storage frame relating to the second embodiment and for explaining a state in which a prism is stored;

FIG. 12 is a sectional view relating to the second embodiment and showing a configuration of a prism storage frame of a modification;

DETAILED DESCRIPTION OF THE PREFERRED EMBODIMENTS

An image pickup unit according to the present invention is explained below. In the following explanation, it should be noted that drawings based on embodiments are schematic and a relation between thicknesses and widths of portions, a ratio of the thicknesses of the respective portions, and the like are different from real ones. In some cases, among the drawings, portions, a relation and a ratio of dimensions of which are different, are included.

First Embodiment

Figure 1:
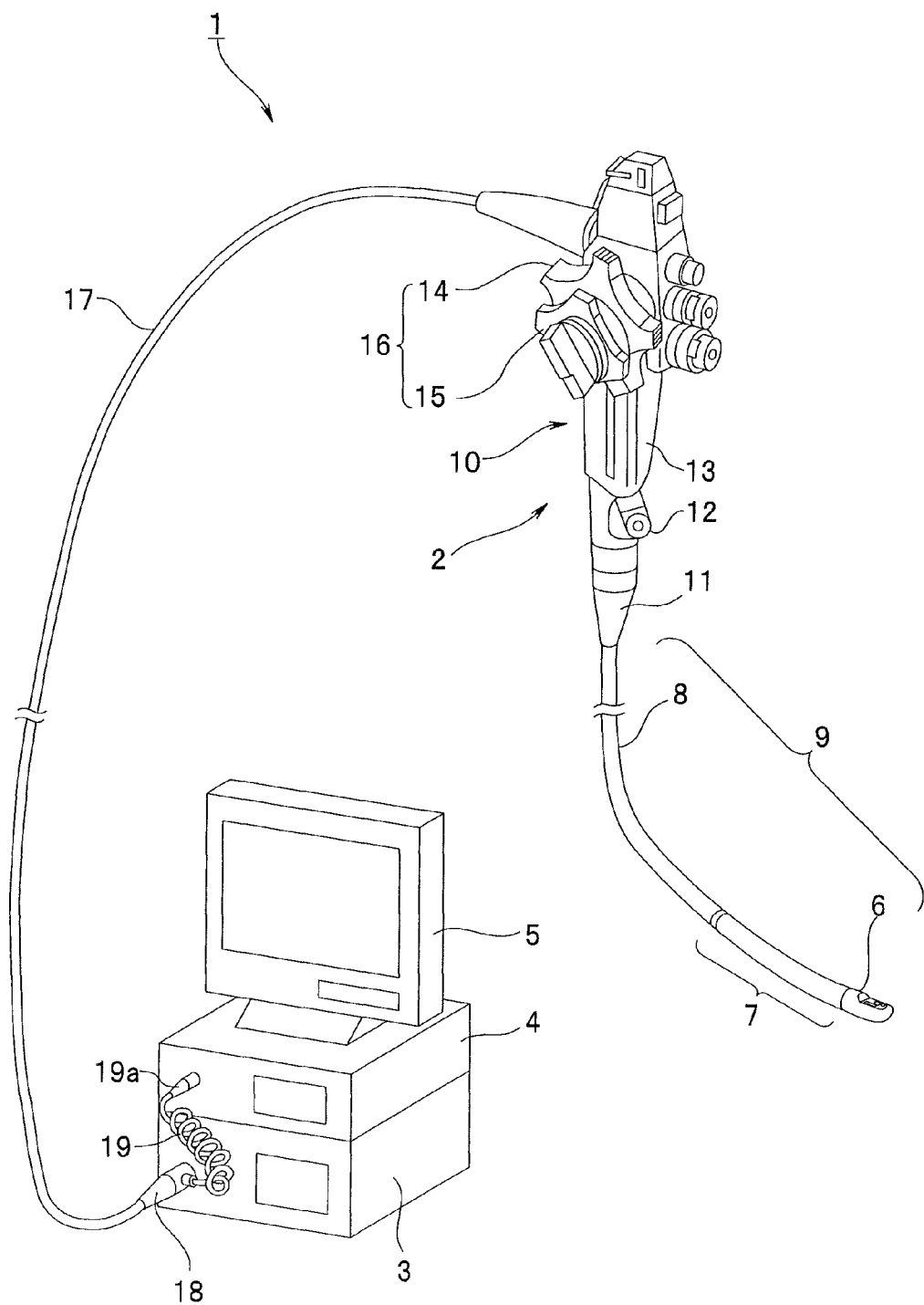
FIG. 1 is a diagram relating to a first embodiment of the present invention and showing a configuration of an electronic endoscope system including an electronic endoscope apparatus of a side-view type.
Figure 2:
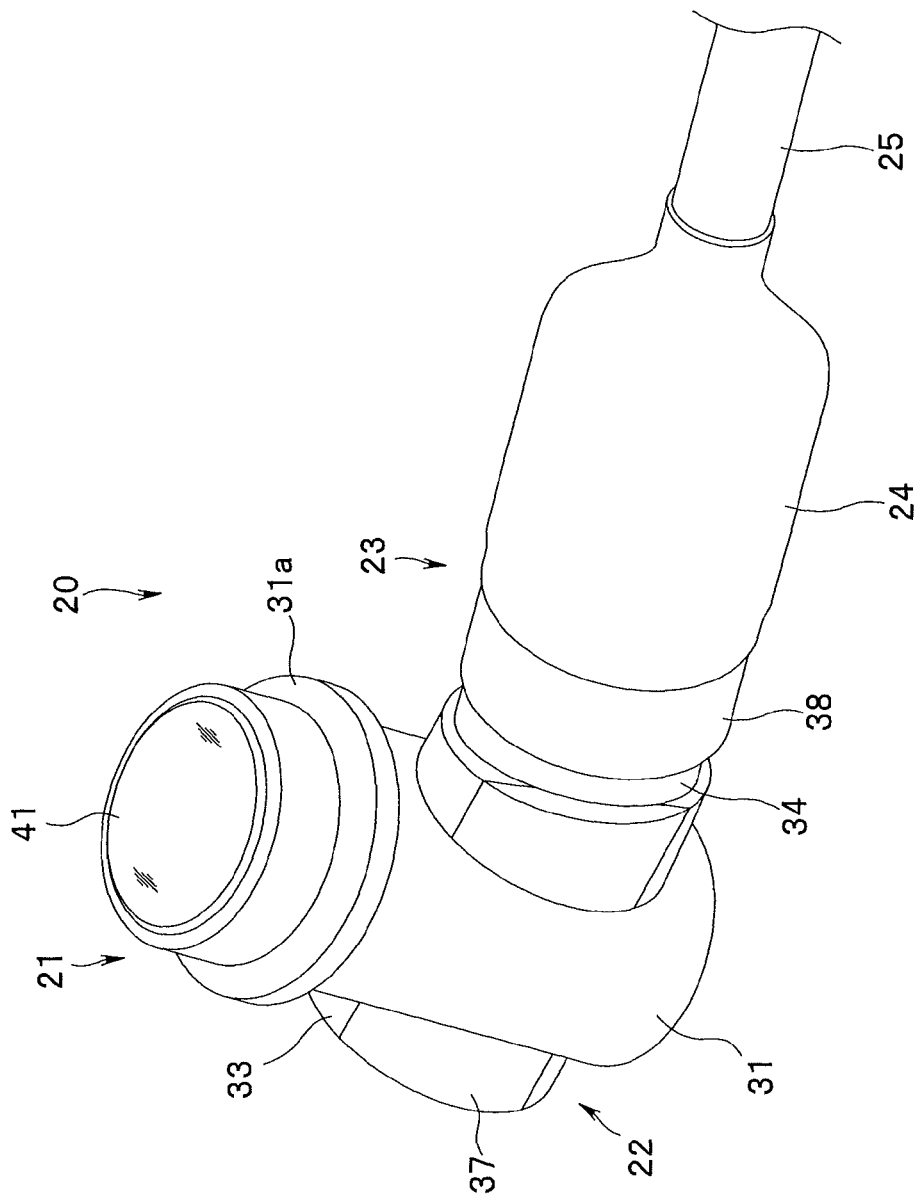
FIG. 2 is a perspective view relating to the first embodiment and showing a configuration of an image pickup unit.
Figure 4:
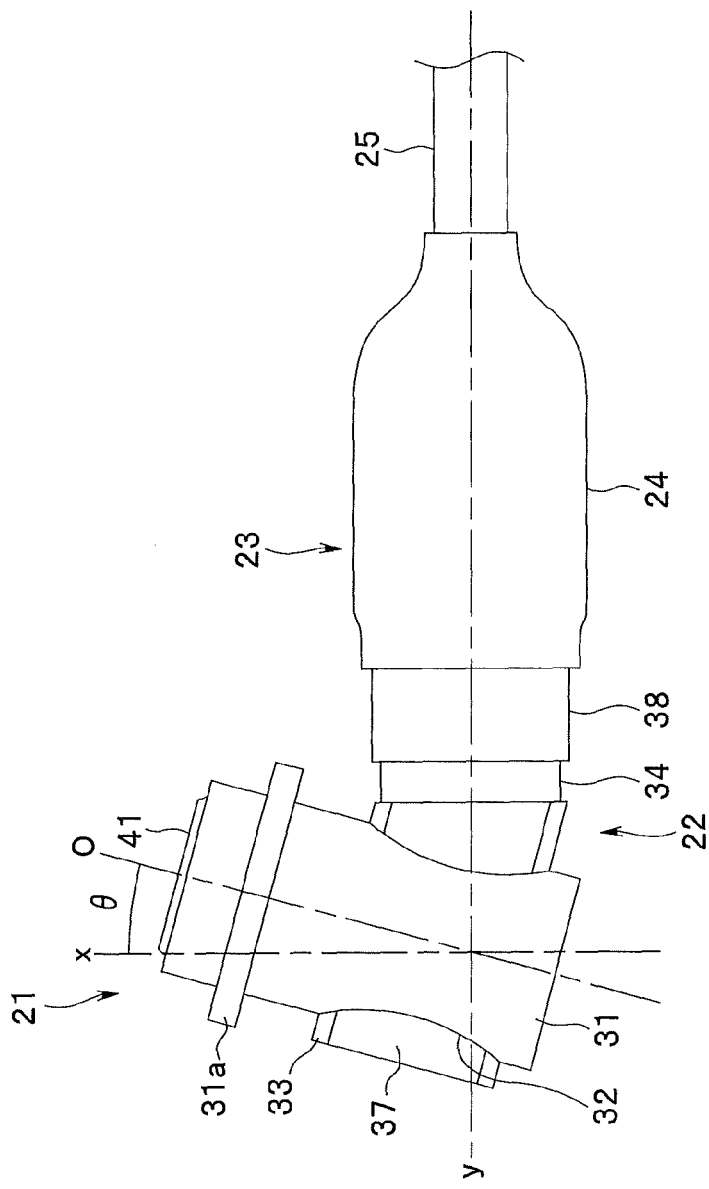
FIG. 4 is a side view relating to the first embodiment and showing the configuration of the image pickup unit.
Figure 3:
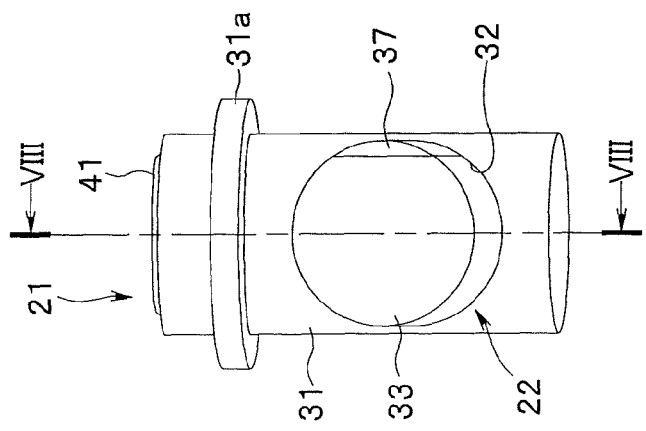
FIG. 3 is a front view relating to the first embodiment and showing the configuration of the image pickup unit.
Figure 5:
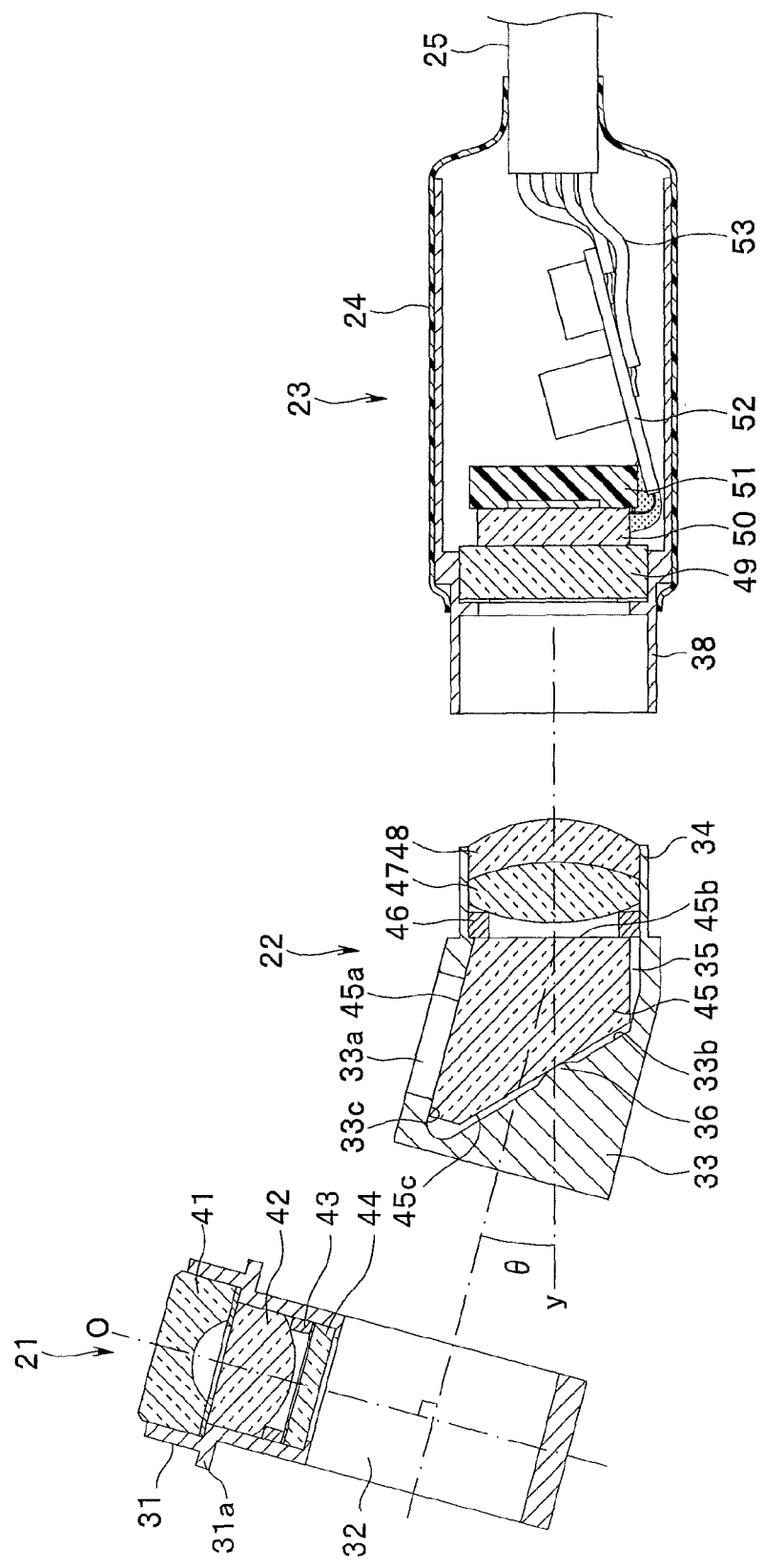
FIG. 5 is a disassembled sectional view relating to the first embodiment and showing the configuration of the image pickup unit.
Figure 6:
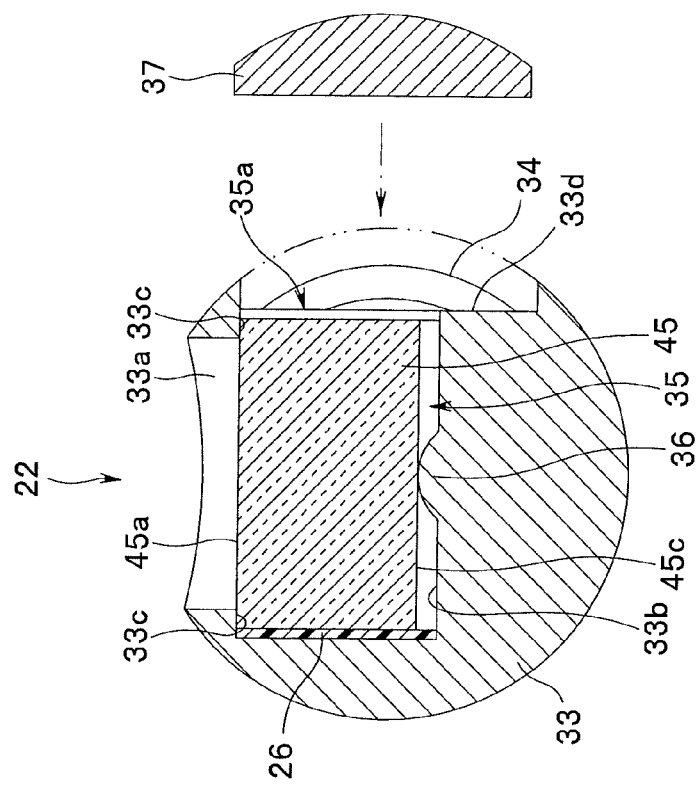
FIG. 6 is a side view relating to the first embodiment and showing a configuration of a prism unit.
Figure 7:
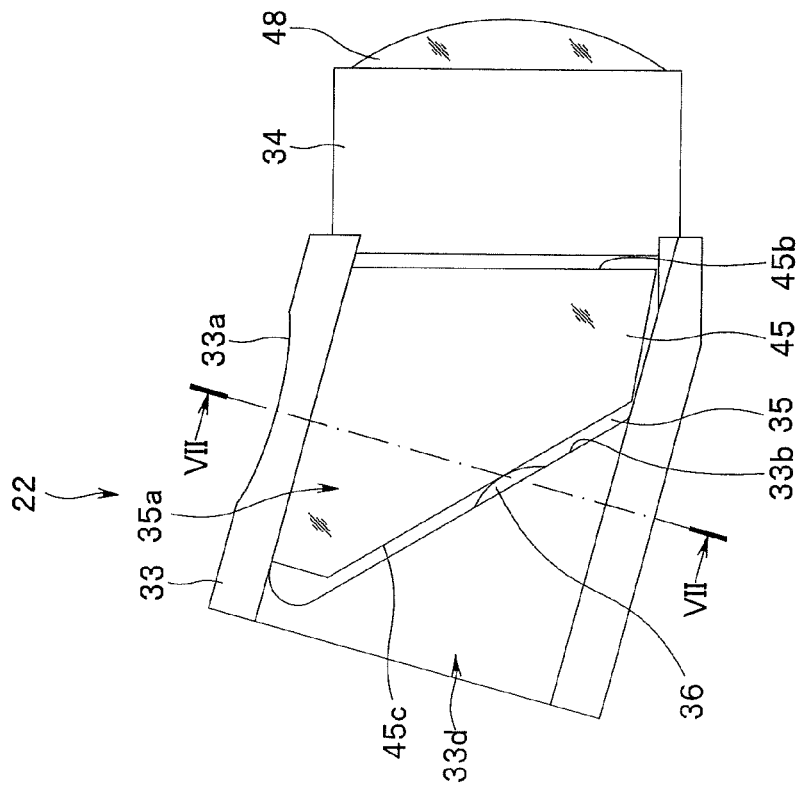
FIG. 7 is a VII-VII sectional view of FIG. 6 relating to the first embodiment.
Figure 8:
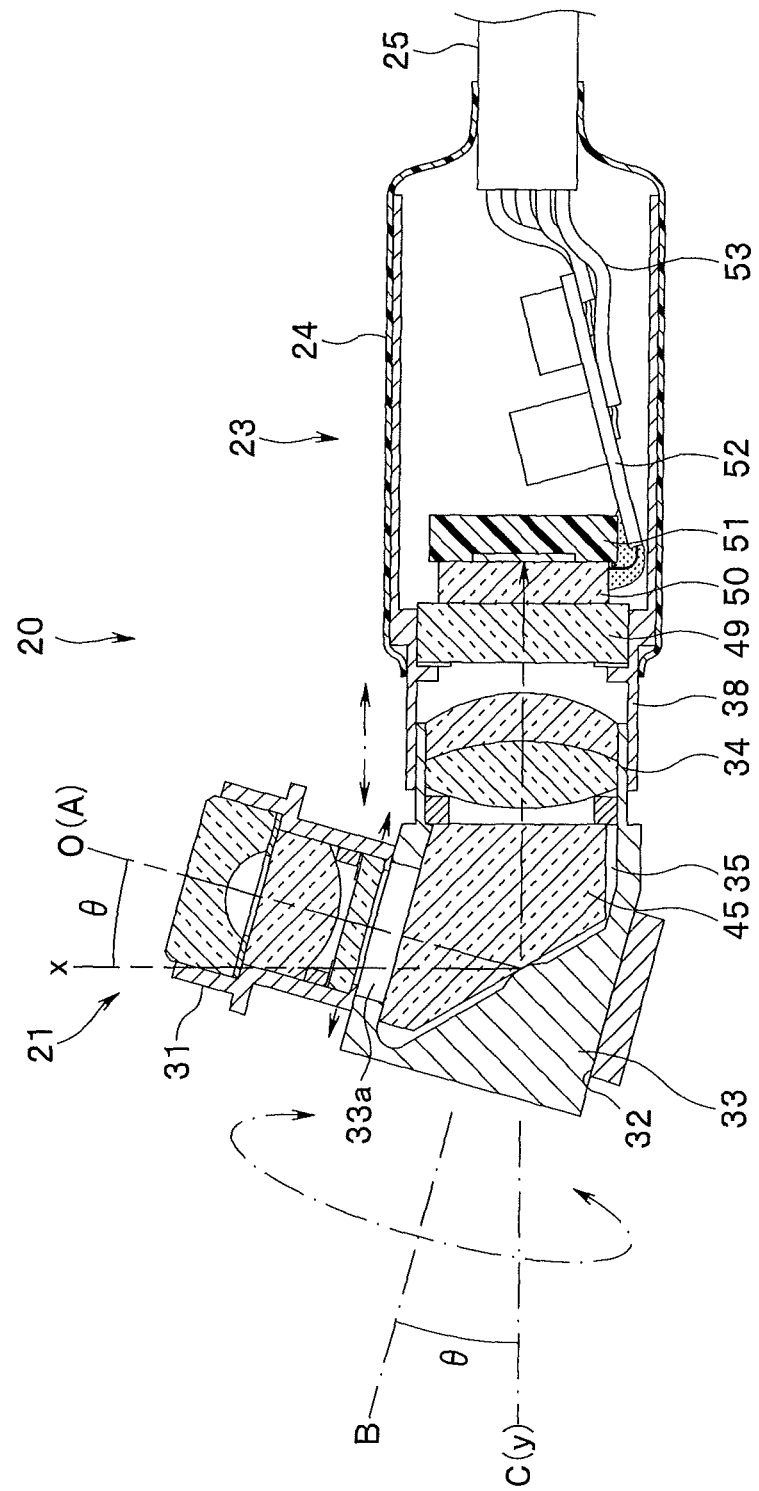
FIG. 8 is a sectional view relating to the first embodiment and showing the configuration of the image pickup unit.

First, a first embodiment of the present invention is explained below on the basis of FIGS. 1 to 8. FIGS. 1 to 8 relate to the first embodiment of the present invention. FIG. 1 is a diagram showing a configuration of an electronic endoscope system including an electronic endoscope apparatus of a side-view type. FIG. 2 is a perspective view showing a configuration of an image pickup unit. FIG. 3 is a front view showing the configuration of the image pickup unit. FIG. 4 is a side view showing the configuration of the image pickup unit. FIG. 5 is a disassembled sectional view showing the configuration of the image pickup unit. FIG. 6 is a side view showing a configuration of a prism unit. FIG. 7 is a VII-VII sectional view of FIG. 6. FIG. 8 is a sectional view showing the configuration of the image pickup unit.

As shown in FIG. 1, an electronic endoscope system 1 according to this embodiment mainly includes an electronic endoscope apparatus 2 of a side-view type, in this embodiment, of a rear oblique-view type, a light source apparatus 3, a video processor 4, and a monitor 5.

The electronic endoscope apparatus 2 includes a long and elongated insertion section 9, an operation section 10, and a universal cable 17, which is an electric cable. The insertion section 9 of the electronic endoscope apparatus 2 includes a distal end portion 6, a bending portion 7, and a flexible tube portion 8 in this order from the distal end.

The operation section 10 includes a posterior orifice portion 11, which is a bending preventing portion, connected to one end of the flexible tube portion 8 of the insertion section 9, a treatment instrument channel insert-through portion 12, which is an opening portion of a treatment instrument channel through which various treatment instruments disposed in the insertion section 9 are inserted, and an operation section main body 13.

In the operation section main body 13, a bending operation knob 16 for bending the bending portion 7 of the insertion section 9 is pivotably provided and switches and the like for various endoscope functions are provided. In the bending operation knob 16, a UD bending operation knob 14 for bending the bending portion 7 in an up down direction and an RL bending operation knob 15 for bending the bending portion 7 in a left right direction are disposed to be superimposed one on top of the other.

The universal cable 17 extended from the operation section 10 includes, at an extension end, an endoscope connector 18 detachably attachable to the light source apparatus 3. The electronic endoscope apparatus 2 according to this embodiment transmits illumination light from the light source apparatus 3 to the distal end portion 6 through a light guide bundle. A coil-like coil cable 19 extends from the endoscope connector 18. An electric connector 19a detachably attachable to the video processor 4 is provided at an extension end of the coil cable 19.

The video processor 4 is electrically connected to the monitor 5 that displays an endoscope image. The video processor 4 applies signal processing to an image pickup signal photoelectrically converted by an image pickup unit 20 explained later of the electronic endoscope apparatus 2 and outputs the image pickup signal to the monitor 5 as an image signal.

Next, a specific configuration of the image pickup unit 20 is explained below on the basis of FIGS. 2 to 8. The image pickup unit 20 is incorporated in the distal end portion 6 of the insertion section 9 in the electronic endoscope apparatus 2.

As shown in FIGS. 2 to 4, the image pickup unit 20 mainly includes a lens unit 21 of first optical system holding means, which is a first optical system holding frame, a prism unit 22 of second optical system holding means, which is a second optical system holding frame, fit in the lens unit 21, and a CCD unit 23, which is image pickup means of third optical system holding means, which is a third optical system holding frame, fit in the prism unit 22. The image pickup unit 20 is an image pickup device of a rear oblique-view type set at a predetermined angle θ (e.g., an angle of 10°) further to a rear with respect to an axis (an axis x in FIG. 4) orthogonal to a longitudinal axis (an insertion axis, an axis y in FIG. 4) of the insertion section 9.

The lens unit 21 includes a front lens holding frame 31 of a substantially cylindrical shape formed of metal or the like, which is a first holding frame. The front lens holding frame 31 has an outward flange 31a formed on an outer circumferential portion on an upper side. A front lens group, which is an object optical system, is disposed on an inside of the front lens holding frame 31. The outward flange 31a of the front lens holding frame 31 is a flange for positioning, although not shown in the figure, the image pickup unit 20 when the image pickup unit 20 is fit in a rigid frame, which is a distal end forming portion, of the distal end portion 6 when the image pickup unit 20 is arranged at the distal end portion 6 of the electronic endoscope apparatus 2.

In an upper opening position of the front lens holding frame 31, a plano-concave lens 41, which is a part of the front lens group and is an object lens, functioning as an observation window exposed at the distal end portion 6 of the electronic endoscope apparatus 2 is fit by an adhesive or the like. In the front lens holding frame 31, as shown in FIG. 5, a plano-convex lens 42 and an optical member 44 such as an optical filter, which are a part of the front lens group, are arranged on an inside and bonded and fixed.

A space tube 43 is provided between the plano-convex lens 42 and an optical member 44. In the front lens holding frame 31, a through-hole portion 32 of a perfect circular shape in cross section having a hole axis in a direction orthogonal to a longitudinal axis (a photographing optical axis O made incident on the front lens group) is formed in a lower position near a position where the optical member 44 is set.

The prism unit 22 functioning as optical path converting means includes a prism storage frame 33, which is a substantially columnar storing means, and a cylindrical rear lens holding frame 34 tilted at a predetermined angle θ (e.g., an angle of 10°) with respect to the prism storage frame 33 and provided continuously from the prism storage frame 33. The prism storage frame 33 and the rear lens holding frame 34 form a second holding frame integrally formed of metal or the like.

The prism storage frame 33 is formed as a recess in order to store a prism 45, an angle formed by an incident surface 45a and an exit surface 45b of which is an obtuse angle, and includes a prism storing section 35 opened in a side circumferential portion. In the prism storage frame 33, a circular opening portion 33a communicating with the prism storing section 35 is formed in an upper position in an outer circumferential portion. The opening portion 33a is a hole portion for leading a photographing light beam made incident on the front lens group of the lens unit 21 to the prism 45.

The prism storage frame 33 has a slope portion 33b that forms the prisms storing section 35. A reflection surface 45c of the prism 45 arranged in the prism storage frame 33 is arranged to be opposed to the slope portion 33b. In substantially the center portion of the slope portion 33b, a substantially semispherical (dome-like) projection 36, which comes into point-contact with and abuts against the reflection surface 45c of the prism 45, is formed.

Further, the prism storage frame 33 has an upper inner surface 33c that forms an entire upper surface of the prism storing section 35. The upper inner surface 33c is a plane formed around the opening portion 33a to come into surface-contact with and abut against the incident surface 45a of the prism 45 arranged in the prism storing section 35. The incident surface 45a of the prism 45 abuts against the upper inner surface 33c only in an area outside the photographing light beam made incident from the lens unit 21. The prism storing section 35 is a recess of a triangular shape in cross section having the slope portion 33b as a slope. The prism storing section 35 is formed in the prism storage frame 33 to communicate with the rear lens holding frame 34.

In the prism storage frame 33, as shown in FIGS. 6 and 7, an opening portion 35a of the prism storing section 35 is provided. The prism storage frame 33 has a recess 33d cut in a concave shape in cross section on a side circumferential portion on one side. In the prism storage frame 33, the prism 45 is inserted and arranged into the prism storing section 35 from the opening portion 35a of the recess 33d. Specifically, the prism 45 is stored and arranged in the prism storing section 35 and assembled to the prism storage frame 33 from the opening portion 35a of the prism storing section 35, which is formed on the side portion of the prism storage frame 33, along a direction orthogonal to the optical axis O of photographing light that reflects and converts the optical path. The recess 33d of the prism storage frame 33 is fit with a cover body 37, which is tabular cover means, having one surface formed in an arcuate shape, such that the cover body 37 close the opening portion 35a of the prism storing section 35 and firmly fixed by an adhesive or the like.

To the prism 45 inserted into and arranged in the prism storing section 35, a UV (ultraviolet curing) adhesive 26 is applied to one side surface. The prism 45 is arranged in the prism storing section 35 from the surface side to which the UV adhesive 26 is applied. Specifically, an ultraviolet ray (UV) is irradiated on a bottom surface portion, which forms the prism storing section 35, on the opposite side of the opening portion 35a of the prism storing section 35 and the UV adhesive 26 from the opening portion 35a side, whereby the prism 45 is firmly fixed in the prism storing section 35.

The prism storage frame 33 with the cover body 37 attached thereto is formed in a columnar shape of a perfect circle in cross section that can be inserted and arranged through the through-hole portion 32 of the front lens holding frame 31. The prism storage frame 33 is set in a perfect circular shape in which the outer diameter of the prism storage frame 33 is equal to the hole diameter of the through-hole portion 32 or the outer diameter of the prism storage frame 33 is slightly smaller than the hole diameter of the through-hole portion 32. In other words, the prism storage frame 33 is configured to be capable of being inserted through and arranged in the through-hole portion 32 of the front lens holding frame 31. The prism storage frame 33 is not limited to the columnar shape and may be formed as, for example, a rectangular body. The through-hole portion 32 of the front lens holding frame 31 may be formed as a hole portion of a rectangular body shape to correspond to the rectangular body.

Referring back to FIG. 5, in the rear lens holding frame 34, a double convex lens 47 forming a rear lens group of an object lens group and a meniscus concave lens 48 joined to the double convex lens 47 are firmly fixed. In the rear lens holding frame 34, a space tube 46 is arranged between the double convex lens 47 and the prism 45 to abut against the double convex lens 47 and the exit surface 45b of the prism 45.

The CCD unit 23 includes a substantially columnar CCD holder 38, which is a third holding frame, and a thermally-shrinkable tube 24 that covers a periphery of the CCD holder 38. A cable 25 is extended rearward from a proximal end portion of the thermally-shrinkable tube 24.

The CCD holder 38 holds an optical component 49 such as an optical filter. A cover glass 50 joined to a proximal end surface of the optical component 49, a CCD 51 of a solid-state image pickup device joined to a proximal end surface of the cover glass 50 and forming image pickup means for detecting and photoelectrically converting photographing light, and a circuit board 52 electrically connected to the CCD 51, with an electronic component mounted thereon are arranged on an inside of the CCD holder 38.

A front surface of the cover glass 50 is firmly fixed with a rear surface of the optical component 49, which is held by the CCD holder 38, by an optical adhesive. A rear surface of the cover glass 50 is firmly fixed with a front surface of the CCD 51 by the optical adhesive to cover a light receiving element of the CCD 51. Plural communication lines 53 disposed in the cable 25 are electrically connected to the circuit board 52 by solder or the like. The solid-state image pickup device is not limited to the CCD 51 and may be a CMOS sensor or the like.

An assembly procedure for the image pickup unit 20 according to this embodiment configured as explained above is explained below.

First, the lens unit 21, the prism unit 22, and the CCD unit 23 are individually assembled.

More specifically, in the lens unit 21, an aperture, the plano-concave lens 41, the plano-convex lens 42, and the optical member 44 are bonded and fixed in predetermined positions of the front lens holding frame 31 (see FIG. 5).

In the assembly of the prism unit 22, first, the UV adhesive 26 is applied to one side surface of the prism 45. The one side surface of the prism 45 is a surface opposed to a bottom surface of the prism storing section 35 when the prism 45 is arranged in the prism storing section 35.

The prism 45 is stored in the prism storing section 35 from the opening portion 35a of the prism storing section 35 formed in the recess 33d of the prism storage frame 33 (see FIGS. 6 and 7). At this point, the prism 45 is stored in the prism storing section 35 with a direction thereof determined in a state in which the incident surface 45a is opposed to the upper inner surface 33c of the prism storage frame 33 and the reflection surface 45c is opposed to the slope portion 33b of the prism storage frame 33. In other words, the prism 45 is stored in the prism storing section 35 in a state in which the incident surface 45a outside the photographing light beam is set in surface-contact with and abutment against the upper inner surface 33c of the prism storage frame 33 and the reflection surface 45c is set in point-contact with and abutment against the projection 36 formed on the slope portion 33b.

Subsequently, the space tube 46, the double convex lens 47, and the meniscus concave lens 48 are dropped into the rear lens holding frame 34 from a proximal end opening of the rear lens holding frame 34. The double convex lens 47 and the meniscus concave lens 48 may be in a state in which the lenses are joined in advance.

The prism 45 is pressed from a rear to a front via the space tube 46, the double convex lens 47, and the meniscus concave lens 48. Consequently, the exit surface 45b of the prism 45 abuts against the space tube 46 and is pressed to the front side.

At this point, the reflection surface 45c of the prism 45 comes into point-contact with the projection 36 formed on the slope portion 33b and is bumped in a state in which the reflection surface 45c receives a pressing force to the front side. The incident surface 45a of the prism 45 is bumped against the upper inner surface 33c of the prism storage frame 33.

Therefore, even if machining variations of the prism 45 or the prism storage frame 33 slightly occur, the prism 45 is in a state in which the reflection surface 45c is set in point-contact with the projection 36 and the incident surface 45a and the upper inner surface 33c of the prism storage frame 33 are surely set in surface-contact and the exit surface 45b and the space tube 46 are surely set in surface-contact. In other words, the prism 45 is stored in the prism storage frame 33 in a state in which the prism 45 is positioned by one-point contact and two-surface contact in the prism storage frame 33.

While this state is kept, an ultraviolet ray (UV) is irradiated via the prism 45 from the opening portion 35a side of the prism storing section 35 formed in the recess 33d of the prism storage frame 33. In this way, while the state in which the incident surface 45a and the upper inner surface 33c of the prism storage frame 33 are surely set in surface-contact and the exit surface 45b and the space tube 46 are surely set in surface-contact is kept, the UV adhesive 26 applied to the side surface is hardened in the prism storing section 35, whereby the prism 45 is firmly fixed to the prism storage frame 33.

The double convex lens 47 and the meniscus concave lens 48 are firmly fixed to the rear lens holding frame 34 by an optical adhesive such as a UV adhesive.

Finally, as shown in FIG. 7, the cover body 37 is fit in and bonded to the recess 33d of the prism storage frame 33. The assembly of the prism unit 22 ends in a state in which a light blocking effect of the prism storing section 35 is secured.

In the CCD unit 23, the aperture, the optical component 49, the cover glass 50, the CCD 51, the circuit board 52, and the cable 25 are assembled to the CCD holder 38. The thermally-shrinkable tube 24 is subjected to heat treatment and contracted to cover an outer circumferential portion of the CCD holder 38 (see FIG. 5). The cover glass 50, the CCD 51, the circuit board 52, and the cable 25 may be assembled in advance before being mounted on the CCD holder 38.

The lens unit 21, the prism unit 22, and the CCD unit 23 assembled as explained above are held and fixed by a jig and are respectively adjusted and assembled in positions where predetermined optical performances are satisfied.

Specifically, as shown in FIG. 8, the prism storage frame 33 of the prism unit 22 is inserted through and arranged in the through-hole portion 32 formed in the front lens holding frame 31 of the lens unit 21. The CCD holder 38 of the CCD unit 23 is inserted over and fit with the rear lens holding frame 34 of the prism unit 22.

Specifically, before being respectively fixed by an adhesive, the lens unit 21 and the prism unit 22 are relatively movable in a direction along a longitudinal axis B of the prism storage frame 33 orthogonal to a longitudinal axis A of the front lens holding frame 31 (the photographing optical axis O made incident on the front lens group) (a direction tilting at a predetermined angle θ with respect to a longitudinal axis C of the CCD holder 38) and is relatively pivotable about the longitudinal axis B.

In other words, the prism storage frame 33 and the front lens holding frame 31 are relatively movable in the direction along the longitudinal axis B of the prism storage frame 33 and is relatively pivotable about the longitudinal axis B.

Before being respectively fixed, the prism unit 22 and the CCD unit 23 are relatively movable along the longitudinal axis C of the CCD holder 38 (the photographing optical axis O reflected by the prism 45 and made incident on the CCD 51).

In other words, the rear lens holding frame 34 and the CCD holder 38 are relatively movable along the longitudinal axis C of the CCD holder 38.

In this way, when the image pickup unit 20 according to this embodiment is assembled, the lens unit 21, the prism unit 22, and the CCD unit 23 are configured to be capable of respectively relatively moving or pivoting.

Specifically, the lens unit 21 and the prism unit 22 are configured to be capable of relatively moving along the longitudinal axis B of the prism storage frame 33 and relatively pivoting about the longitudinal axis B. Therefore, fixing positions of the lens unit 21 and the prism unit 22 can be finely adjusted. Adjustment of a deflection angle and an angle of view of an observation image can be easily performed. In positions of a deflection angle and an angle of view that satisfy predetermined optical performance, the prism storage frame 33 of the prism unit 22 and the front lens holding frame 31 of the lens unit 21 are positioned and fixed by a jig. The lens unit 21 and the prism unit 22 are firmly fixed by a thermosetting adhesive.

Since the prism unit 22 and the CCD unit 23 are configured to be capable of relatively moving along the longitudinal axis C of the CCD holder 38, fixing positions of the prism unit 22 and the CCD unit 23 can be finely adjusted and focus adjustment for an observation image can be easily performed. In a focus position that satisfies the predetermined optical performance, the rear lens holding frame 34 of the prism unit 22 and the CCD holder 38 of the CCD unit 23 are positioned and fixed by a jig. The prism unit 22 and the CCD unit 23 are firmly fixed by the thermosetting adhesive. The deflection angle adjustment, the adjustment of the angle of view, and the focus adjustment can be simultaneously carried out.

As explained above, the image pickup unit 20 according to this embodiment includes the prism 45. Even if machining variations of the prism 45 and the holding frames that hold the optical section occur, it is possible to simultaneously perform the adjustment of the deflection angle, the angle of view, and the focus of the observation image by adjusting the fixing positions of the units 21, 22, and 23. Further, in the image pickup unit 20, when the prism 45 is stored and fixed in the prism storage frame 33, positioning of the prism 45 in the prism storage frame 33 can be easily performed. It is unnecessary to adjust setting of the prism 45 in order to satisfy the predetermined optical performance. In the prism storage frame 33, the opening portion 35a of the prism storing section 35 is formed on the side portion such that the prism 45 can be stored and arranged from a side portion direction (the direction orthogonal to the optical axis O of the photographing light reflected by the prism 45). Therefore, it is possible to easily perform positioning for bringing the reflection surface 45c of the prism 45 into point-contact with the projection 36 and bringing the incident surface 45a into surface-contact with the upper inner surface 33c of the prism storage frame 33.

Consequently, efficiency of assemblability of the image pickup unit 20 is improved and productivity of the image pickup unit 20 is stabilized. As a result, the number of defective products that do not satisfy optical performance during manufacturing decreases and yield of the image pickup unit 20 is remarkably improved.

Further, the image pickup unit 20 is the rear oblique-view type. The prism 45 in which an angle formed by the incident surface 45a and the exit surface 45b is an obtuse angle is used. In an image pickup unit in the past of such a rear oblique-view type, an effective diameter of a ray tends to increase on an exit surface side of a prism. On the other hand, the image pickup unit 20 according to this embodiment has the configuration of the prism unit 22 separated from the lens unit 21. The prism 45 can be stored in the prism storing section 35 from the side portion of the prism storage frame 33. Therefore, it is possible to prevent an increase in size of the prism storage frame 33.

In the prism 45 according to this embodiment, the angle formed by the incident surface 45a and the exit surface 45b is set to an obtuse angle (90°+θ, e.g., an angle of 100°) obtained by adding the predetermine angle θ (e.g., an angle of 10°) to a right angle (an angle of 90°). This is for the purpose of making photographing light from the lens unit 21 vertically incident on the incident surface 45a and causing the photographing light reflected by the reflection surface 45c to vertically exit from the exit surface 45b. As explained above, in the state in which the reflection surface 45c is in-point contact with the projection 36, the prism 45 is arranged in the prism storage frame 33 in the state in which the incident surface 45a and the upper inner surface 33c of the prism storage frame 33 are surely in surface-contact and the exit surface 45b and the space tube 46 are surely in surface-contact. Consequently, the incident surface 45a of the prism 45 is kept substantially perpendicular to the photographing optical axis O made incident from the front lens group of the lens unit 21. The exit surface 45b of the prism 45 is kept substantially perpendicular to the photographing optical axis O reflected on the reflection surface 45c. Therefore, variations in an oblique-view angle and optical performance can be generally compensated by machining accuracy of the prism 45.

As the image pickup unit according to this embodiment, the rear oblique-view type of the side-view type is explained as the example. However, the image pickup unit is not limited thereto. It goes without saying that the image pickup unit can also be applied to, for example, a front oblique-view type and a side-view type in which a photographing optical path conversion angle by the prism 45 is 90°.

Second Embodiment

Next, an image pickup unit according to a second embodiment is explained blow on the basis of FIGS. 9 to 12.

FIGS. 9 to 12 relate to the second embodiment of the present invention. FIG. 9 is a front view showing the configuration of the image pickup unit. FIG. 10 is a sectional view showing the configuration of the image pickup unit along X-X in FIG. 9. FIG. 11 is a sectional view of a prism storage frame for explaining a state in which a prism is stored. FIG. 12 is a sectional view showing a configuration of a prism storage frame of a modification. In the following explanation, components same as the components in the first embodiment are denoted by the same reference numerals and signs for convenience of the explanation. Detailed explanation of the components and operational effects of the components are omitted.

The image pickup unit 20 according to this embodiment is a side-view type including the prism 45, which is optical path converting means for reflecting photographing light at an angle of 90° and converting an optical path. As shown in FIGS. 9 and 10, the prism storage frame 33 of the prism unit 22 fit in the front lens holding frame 31 of the lens unit 21 is a rectangular body. When the prism storage frame 33 is formed as the rectangular body, there is an advantage that an external shape can be reduced in size. The through-hole 39 formed in the front lens holding frame 31 is also a hole portion of a rectangular body shape to correspond to the prism storage frame 33. As in the first embodiment, it goes without saying that the prism storage frame 33 may be formed in a columnar shape and the through-hole 39 may be formed as a hole portion of a columnar shape to correspond to the prism storage frame 33.

Since the image pickup unit 20 is the side-view type, in the prism unit 22 according to this embodiment, axes of the prism storage frame 33 and the rear lens holding frame 34 are formed in a linear shape. In other words, the lens unit 21 and the prism unit 22 are fit with each other in a state in which longitudinal axes thereof are orthogonal to each other. In FIG. 10, although not shown, the CCD unit 23 has a configuration same as the configuration in the first embodiment.

In a state in which the prism 45 according to this embodiment is arranged in the prism storing section 35 of the prism storage frame 33, the prism 45 is in a state in which an area on the exit surface 45b outside a photographing light beam reflected on the reflection surface 45c is in surface-contact with and bumped against a proximal end inner surface 61 of the prism storage frame 33 that forms the prism storing section 35. In a proximal end inner circumferential portion of the prism storage frame 33, an inward flange 62 projecting inward is formed. A front end face of the inward flange 62 forms the proximal end inner surface 61.

The prism 45 is in a state in which the exit surface 45b is in surface-contact with and bumped against a space tube 56 dropped into an upper opening of the prism storage frame 33. In the prism storage frame 33, a tabular optical member 57 such as an optical filter is disposed on an upper side of the space tube 56.

A projection 55 that comes into line-contact with the reflection surface 45c of the prism 45 is provided on the slope portion 33b of the prism storage frame 33. In other words, the projection 55 in this embodiment is formed in a so-called semicylindrical shape obtained by cutting a cylinder in a longitudinal direction and is configured to project to swell over the slope portion 33b (see FIGS. 10 and 11). Consequently, the projection 55 comes into line-contact with and abuts against the reflection surface 45c of the prism 45.

In the prism storage frame 33, as shown in FIG. 11, the recess 33d in which the prism storing section 35 is opened is formed on a side surface. The prism 45 with the UV adhesive 26 applied on one side surface thereof is stored in the prism storing section 35 from the opening portion 35a side of the prism storing section 35 provided in the recess 33d.

Specifically, the prism 45 is stored in the prism storing section 35 with a direction thereof determined in a state in which the exit surface 45b is opposed to the proximal end inner surface 61 of the prism storage frame 33 and the reflection surface 45c is opposed to the slope portion 33b of the prism storage frame 33. In other words, the prism 45 is stored in the prism storing section 35 in a state in which the exit surface 45b is set in surface-contact with and abutment against the proximal end inner surface 61 of the prism storage frame 33 and the reflection surface 45c is set in line-contact with and abutment against the projection 55 formed on the slope portion 33b.

Subsequently, the space tube 56 and the optical member 57 are dropped into the prism storage frame 33 from the upper opening of the prism storage frame 33. The prism 45 is pressed from up to down via the space tube 56 and the optical member 57. Consequently, the incident surface 45a of the prism 45 abuts against the space tube 56 and pressed to the lower side.

At this point, the reflection surface 45c of the prism 45 comes into line-contact with the projection 55 formed on the slope portion 33b and is bumped in a state in which the reflection surface 45c receives a pressing force to the lower side. The exit surface 45b of the prism 45 is bumped against the proximal end inner surface 61 of the prism storage frame 33.

As in the first embodiment, even if machining variations of the prism 45 or the prism storage frame 33 slightly occur, the prism 45 is in a state in which the reflection surface 45c is set in line-contact with the projection 55 and the exit surface 45b and the proximal end inner surface 61 of the prism storage frame 33 are surely set in surface-contact and the incident surface 45a and the space tube 56 are surely set in surface-contact. In other words, the prism 45 is stored in the prism storage frame 33 in a state in which the prism 45 is positioned by one-line contact and two-surface contact in the prism storage frame 33.

While this state is kept, an ultraviolet ray (UV) is irradiated via the prism 45 from the opening portion 35a side of the prism storing section 35 formed in the recess 33d of the prism storage frame 33. In this way, while the state in which the exit surface 45b and the proximal end inner surface 61 of the prism storage frame 33 are surely set in surface-contact and the incident surface 45a and the space tube 56 are surely set in surface-contact is kept, the UV adhesive 26 applied to the side surface is hardened in the prism storing section 35, whereby the prism 45 is firmly fixed to the prism storage frame 33. The double convex lens 47 and the meniscus concave lens 48 are dropped into the rear lens holding frame 34 from the proximal end opening of the rear lens holding frame 34. The double convex lens 47 and the meniscus concave lens 48 are firmly fixed to the rear lens holding frame 34 by an optical adhesive such as a UV adhesive.

With the configuration explained above, the image pickup unit 20 according to this embodiment has effects same as the effects of the first embodiment. In particular, efficiency of assemblability of the image pickup unit 20 is improved and productivity of the image pickup unit 20 is stabilized. As a result, the number of defective products that do not satisfy optical performance during manufacturing decreases and yield of the image pickup unit 20 is remarkably improved. As the image pickup unit according to this embodiment, the side-view type is explained as the example. However, the image pickup unit is not limited thereto. It goes without saying that the image pickup unit can also be applied to, for example, a front oblique-view type and a rear oblique-view type.

As shown in FIG. 12, a substantially semispherical (dome-like) projection 65 may be provided on an inner side surface that is bonded and fixed to a side surface of the prism 45 and forms the prism storing section 35 of the prism storage frame 33. Since the projection 65 is provided on the inner side surface of the prim storage frame 33, the UV adhesive 26 accumulates in a space formed by bringing the side surface of the prism 45 and the projection 65 into point-contact with each other. In other words, by adopting such a configuration, the excessive UV adhesive 26 is prevented from adhering to a portion in the prism 45 where a photographing light beam passes.

Third Embodiment

Next, an image pickup unit according to a third embodiment is explained below on the basis of FIGS. 13 and 14.

Figure 14:
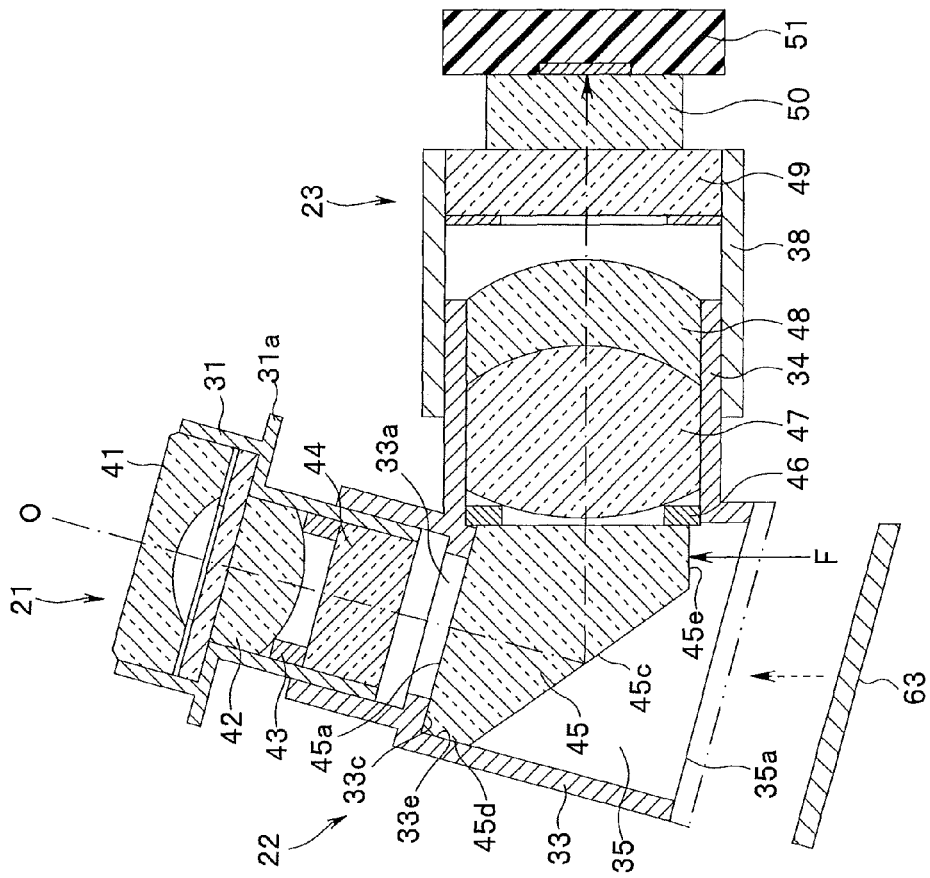
FIG. 14 is a sectional view relating to the third embodiment and showing a configuration of an image pickup unit.
Figure 13:
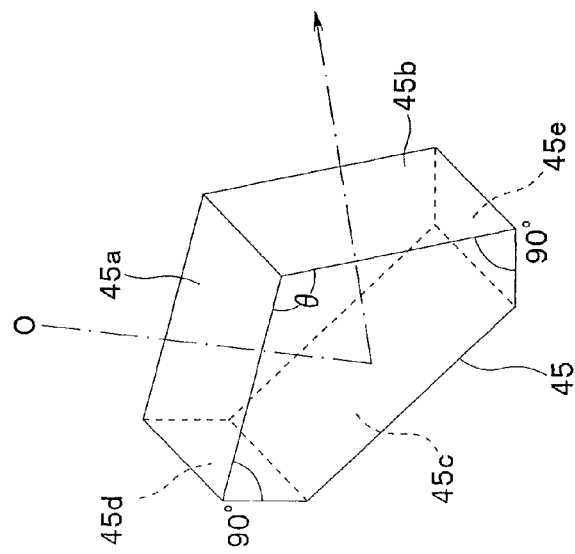
FIG. 13 is a perspective view relating to a third embodiment of the present invention and showing a configuration of a prism.

FIGS. 13 and 14 relate to the third embodiment of the present invention. FIG. 13 is a perspective view showing a configuration of a prism. FIG. 14 is a sectional view showing a configuration of an image pickup unit. In the following explanation, components same as the components in the first embodiment are denoted by the same reference numerals and signs for convenience of the explanation. Detailed explanation of the components and operational effects of the components are omitted.

As shown in FIG. 13, the prism 45 according to this embodiment is a heptahedron and is a triangular prism in which an angle θ formed by the incident surface 45a and the exit surface 45b has, for example, 100°

Figure 15:
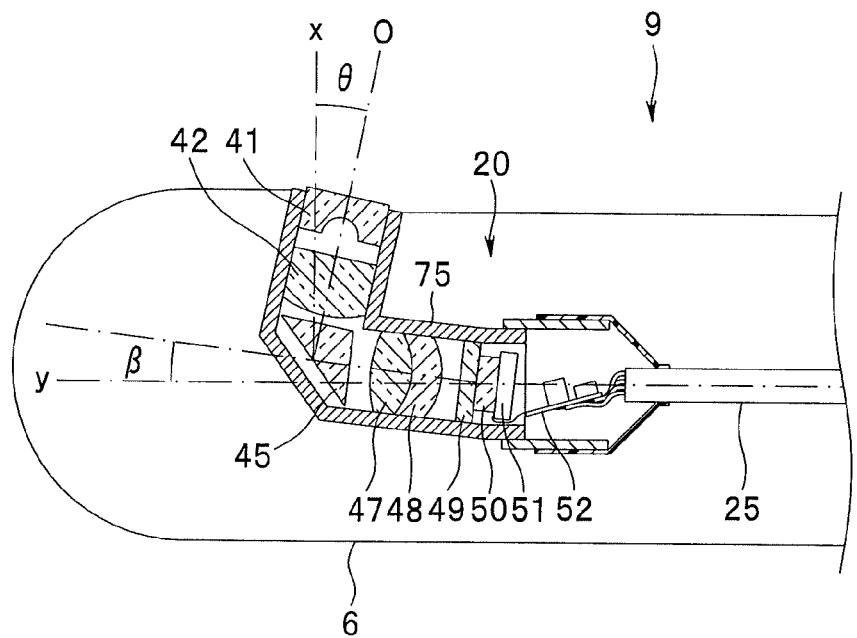
FIG. 15 is a partial sectional view relating to a fourth embodiment of the present invention and showing a state in which an image pickup unit of a rear oblique-view type is arranged at a distal end portion.

In the prism 45, a first surface 45d formed as a plane to the reflection surface 45c while having an angle of a right angle (90°) with respect to the incident surface 45a and a second surface 45e formed as a plane to the reflection surface 45c while having an angle of the right angle (90°) with respect to the exit surface 45b are formed. As shown in FIG. 15, the prism 45 configured in this way is arranged in the prism unit 22 of the image pickup unit 20.

The image pickup unit 20 according to this embodiment is the rear oblique-view type. The lens unit 21 is inserted into and fit in a tubular section provided on the upper side of the prism unit 22.

In the prism storage frame 33 of the prism unit 22, the opening portion 35a of the prism storing section 35 is provided in a lower part. The prism storage frame 33 includes a cover body 63 that closes the opening portion and blocks light. In the prism storage frame 33, the prism 45 is stored in the prism storing section 35 from the opening portion 35a provided in the lower part.

Specifically, the prism 45 is stored to be faced to the inside of the prism storing section 35 from the incident surface 45a side such that the exit surface 45b faces a proximal end side of the prism storage frame 33. At this point, in the prism 45, the second surface 45e perpendicular to the exit surface 45b is pressed in a direction of the incident surface 45a. Therefore, the incident surface 45a comes into surface-contact with and abuts against the upper inner surface 33c that forms one surface of the prism storing section 35. The first surface 45d is bumped against an inner surface of the prism storage frame 33, which is a reference surface 33e that forms one side surface of the prism storing section 35. The reference surface 33e is formed as a plane in the prism storage frame 33 such that an angle formed by the reference surface 33e and the upper inner surface 33c is a right angle (90°) to set the reference surface 33e in surface-contact with the first surface 45d of the prism 45.

In this way, the incident surface 45*a* is bumped against the upper inner surface 33*c*, the first surface 45*d* is bumped against the reference surface 33*e* and positioned, and the prism 45 is bonded and fixed in the prism storing section 35 of the prism storage frame 33. In other words, the prism 45 is positioned in a state in which the two surfaces, i.e., the incident surface 45*a* and the first surface 45*d* are in surface-contact with and abut against the inner surface of the prism storage frame 33.

Finally, the cover body 63 is bonded and fixed to the prism storage frame 33 to close the opening portion 35*a* and a light blocking effect is secured. The optical systems are firmly fixed in the prism storage frame 33 by a thermosetting adhesive or the like.

As explained above, in the image pickup unit 20 according to this embodiment, it is possible to simultaneously bump the incident surface 45*a* and the first surface 45*d* against the upper inner surface 33*c* and the reference surface 33*e*, respectively, simply by pressing the second surface 45*e*. Therefore, it is possible to easily and accurately position the prism 45 in the prism storage frame 33 and store and arrange the prism 45.

Fourth Embodiment

An image pickup unit according to a fourth embodiment is explained below on the basis of FIGS. 15 to 18.

Figure 16:
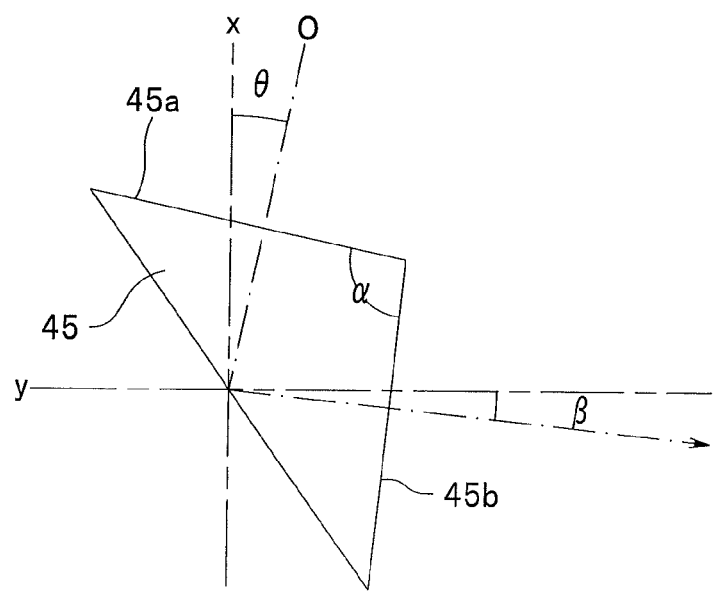
FIG. 16 is a plan view relating to the fourth embodiment and showing a configuration of a prism in the image pickup unit shown in FIG. 15.
Figure 17:
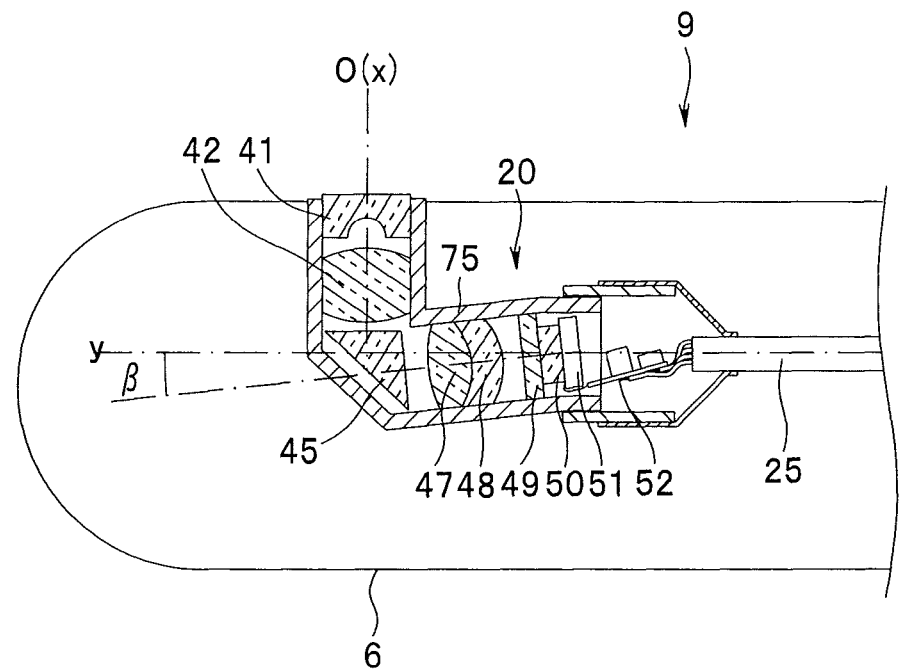
FIG. 17 is a partial sectional view relating to the fourth embodiment and showing a state in which an image pickup unit of a side-view type is arranged at the distal end portion.
Figure 18:
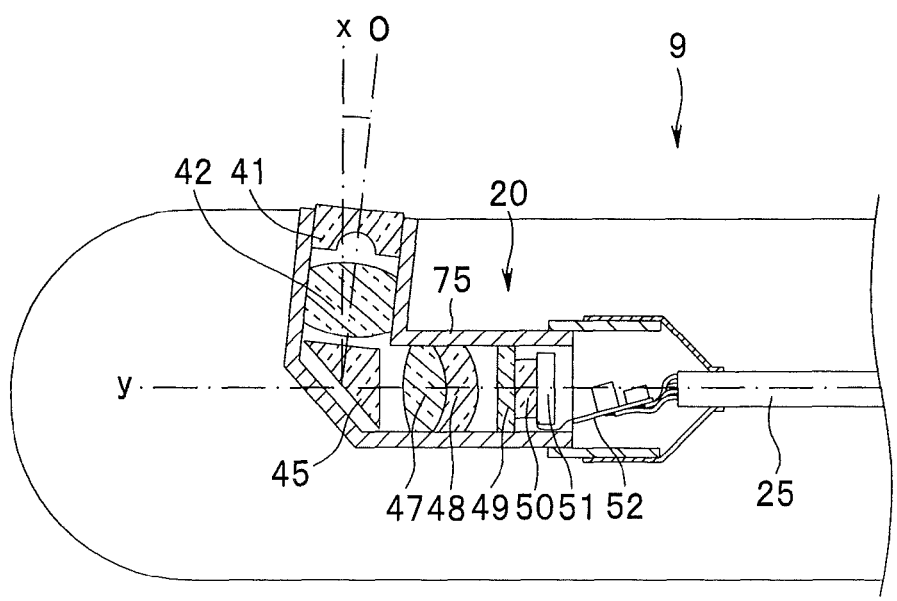
FIG. 18 is a partial sectional view relating to the fourth embodiment and showing a state in which an image pickup unit of a rear oblique-view type having an angle different from an angle shown in FIG. 16 is arranged at the distal end portion.

FIGS. 15 to 18 relate to the fourth embodiment of the present invention. FIG. 15 is a partial sectional view showing a state in which an image pickup unit of a rear oblique-view type is arranged at a distal end portion. FIG. 16 is a plan view showing a configuration of a prism in the image pickup unit shown in FIG. 15. FIG. 17 is a partial sectional view showing a state in which an image pickup unit of a side-view type is arranged at the distal end portion. FIG. 18 is a partial sectional view showing a state in which an image pickup unit of a rear oblique-view type having an angle different from an angle shown in FIG. 16 is arranged at the distal end portion. In the following explanation, components same as the components in the first embodiment are denoted by the same reference numerals and signs for convenience of the explanation. Detailed explanation of the components and operational effects of the components are omitted.

As shown in FIG. 15, the image pickup unit 20 according to this embodiment is the rear oblique-view type. The image pickup unit 20 is arranged at the distal end portion 6 of the insertion section 9 of the electronic endoscope apparatus 2.

A line of sight direction of the image pickup unit 20 is set to be tilted rearward at a predetermined angle θ with respect to an axis x direction orthogonal to an insertion axis (a longitudinal axis) y of the insertion section 9. The double convex lens 47, the meniscus concave lens 48, the optical component 49, the cover glass 50, and the CCD 51, which are a rear lens group, are arranged to be tilted at a predetermined angle β with respect to the insertion axis y. In the image pickup unit 20, the plano-concave lens 41 and the plano-convex lens 42, which are a front lens group, are arranged to be tilted at the predetermined angle θ with respect to the axis x direction. The lenses 41, 42, 47, and 48, the prism 45, the optical component 49, the cover glass 50, and the CCD 51 are integrally held by a holding frame 75.

In the prism 45 disposed in the image pickup unit 20, as shown in FIG. 16, an angle formed by the incident surface 45*a* and the exit surface 45*b* is α and a line of sight direction is set to be tilted rearward at the predetermined angle θ with respect to the axis x direction orthogonal to the insertion axis y of the insertion section 9 (see FIG. 1). In this state, the prism 45 is optically set such that the photographing optical axis O made incident from the incident surface 45*a* and reflected on the reflection surface 45*c* is tilted at the predetermined angle β with respect to the insertion axis y of the insertion section 9 after the reflection.

In FIG. 16, for example, the formed angle α of the prism 45 is set to an angle of 96° and the predetermined angle β is set to an angle of 6°. The image pickup unit 20 is assembled to the distal end portion 6 such that the predetermined angle θ in the line of sight direction is an angle of 12° (an angle of 102° with respect to the insertion axis y).

In other words, the prism 45 is set such that the predetermined angle β (β=6°) is smaller than the predetermined angle θ (θ=12°) (θ>β). Compared with a case in which a right-angle prism (α=90°) is used in the image pickup unit 20 of the rear oblique-view type, the predetermined angle β can be set small in the prism 45. Therefore, it is possible to reduce a size of the entire image pickup unit 20 and reduce an outer diameter of the distal end portion 6 of the insertion section 9.

Therefore, the prism 45 according to this embodiment is set such that, for example, a relation among the formed angle α, the predetermined angle θ, and the predetermined angle β is α−90°=θ−β.

The lenses and the prism 45 are configured as explained above. Therefore, it is possible to use, without changing the outer diameter of the distal end portion 6, the image pickup unit 20 according to this embodiment in the electronic endoscope apparatuses 2 having different line of sight directions such as a front-view type shown in FIG. 17 in which the predetermined angle θ in the line of sight direction is an angle of 0 (zero)° (an angle of 90° with respect to the insertion axis y) and a rear oblique-view type shown in FIG. 18 in which the predetermined angle θ in the line of sight direction is an angle of 6° (an angle of 96° with respect to the insertion axis y).

The invention described above is not limited to the embodiments. Besides, in an implementation stage, various modifications can be carried out without departing from the spirit of the invention. Further, the embodiments include inventions in various stages. Various inventions can be extracted according to appropriate combinations in the plural constituent features disclosed herein.

For example, if the effects explained above can be obtained for deficiencies to be solved by the invention even if several constituent features are deleted from all the constituent features explained in the embodiments, a configuration from which the constituent features are deleted can be extracted as an invention.

What is claimed is:

1. An image pickup unit comprising:
   a first optical system holding frame configured to hold a first object lens group;
   a second optical system holding frame fit in the first optical system holding frame and configured to hold a second object lens group and store a prism that reflects photographing light made incident on the first object lens group and subjects the photographing light to optical path conversion; and
   a third optical system holding frame fit in the second optical system holding frame and configured to hold an image pickup device that detects the photographing light subjected to the optical path conversion by the prism and photoelectrically converts the photographing light, wherein,
   the first optical system holding frame has a hole axis orthogonal to an optical axis of the photographing light made incident on the first object lens group, and a through-hole portion through which the second optical system holding frame can be inserted and arranged is formed in the first optical system holding frame, and the first optical system holding frame and the second optical system holding frame are set relatively movable in a direction orthogonal to the optical axis of the photographing light made incident on the first object lens group, and the second optical system holding frame and the third optical system holding frame are set relatively movable in a direction along the optical axis of the photographing light made incident on the solid-state image pickup device such that predetermined optical performance adjustment can be performed during assembly.

2. The image pickup unit according to claim 1, wherein the through-hole portion is formed in a perfect circular shape in cross section, a fitting region of the second optical system holding frame fit in the first optical system holding frame is formed in a columnar shape that can be inserted into and fit in the through-hole portion, and the first optical system holding frame and the second optical axis holding frame are relatively pivotable.

3. The image pickup unit according to claim 1, wherein the second optical system holding frame includes a prism storage frame in which the prism is stored, and the image pickup unit further comprises:

a prism storing section formed in the prism storage frame and including an opening portion on a side portion of the prism storage frame such that the prism can be stored from a direction orthogonal to an optical axis of the photographing light; and a cover body fit in the prism storage frame to cover the opening portion.

4. The image pickup unit according to claim 3, wherein the prism storage frame has a projection in a slope portion of the prism storage frame to which a reflection surface of the prism is arranged to be opposed, and the prism is stored in the prism storing section in a state in which an area outside a light beam of an incident surface or an area outside the light beam of an exit surface is in contact with an inner surface of the prism storage frame and the reflection surface is in contact with the projection and positioned.

5. The image pickup unit according to claim 4, wherein an angle formed by the incident surface and the reflection surface of the prism is an obtuse angle.

6. The image pickup unit according to claim 3, wherein an ultraviolet ray is irradiated on the prism from the opening portion of the prism storage frame, and one side surface arranged to be opposed to a bottom surface of the prism storing section is firmly fixed in the prism storage frame by an ultraviolet curing adhesive.

7. An image pickup unit comprising:

first holding means for holding a first object lens group;

second holding means fit in the first holding means and for holding a second object lens group and storing optical path converting means for reflecting photographing light made incident on the first object lens group and subjecting the photographing light to optical path conversion; and third holding means fit in the second holding means and for holding image pickup means for detecting the photographing light subjected to the optical path conversion by the optical path converting means and photoelectrically converting the photographing light, wherein the first holding means has a hole axis orthogonal to an optical axis of the photographing light made incident on the first object lens group, and a through-hole portion through which the second holding means can be inserted and arranged is formed in the first holding means and, the first holding means and the second holding means are set relatively movable in a direction orthogonal to the optical axis of the photographing light made incident on the first object lens group and the second holding means and the third holding means are set relatively movable in a direction along the optical axis of the photographing light made incident on the image pickup means such that predetermined optical performance adjustment can be performed during assembly.

* * * * *